United States Patent
Ahola et al.

(10) Patent No.: US 10,337,749 B2
(45) Date of Patent: Jul. 2, 2019

(54) ULTRAVIOLET LIGHT SYSTEM

(71) Applicant: BioZone Scientific International, Inc., Orlando, FL (US)

(72) Inventors: Ari Ahola, Windermere, FL (US); Adam T. Anthony, Windermere, FL (US); Matthew Mercier, Windermere, FL (US)

(73) Assignee: BioZone Scientific International, Inc., Orlando, FL (US)

( * ) Notice: Subject to any disclaimer, the term of this patent is extended or adjusted under 35 U.S.C. 154(b) by 190 days.

(21) Appl. No.: 15/678,930

(22) Filed: Aug. 16, 2017

(65) Prior Publication Data
US 2019/0056123 A1    Feb. 21, 2019

(51) Int. Cl.
| | |
|---|---|
| A61L 9/20 | (2006.01) |
| B01D 45/08 | (2006.01) |
| B01D 46/00 | (2006.01) |
| F24F 3/16 | (2006.01) |
| F24C 15/20 | (2006.01) |
| B01D 53/00 | (2006.01) |

(52) U.S. Cl.
CPC .............. *F24F 3/1603* (2013.01); *A61L 9/20* (2013.01); *B01D 45/08* (2013.01); *B01D 46/0027* (2013.01); *B01D 53/007* (2013.01); *F24C 15/20* (2013.01); *F24C 15/2021* (2013.01); *F24C 15/2028* (2013.01); *F24C 15/2035* (2013.01); *F24F 2003/1667* (2013.01)

(58) Field of Classification Search
CPC ....... A61L 9/20; B01D 45/08; B01D 46/0027; B01D 46/0028
USPC ................... 96/224; 55/DIG. 36; 422/124
See application file for complete search history.

(56) References Cited

U.S. PATENT DOCUMENTS

| | | | |
|---|---|---|---|
| 6,878,195 | B2 | 4/2005 | Gibson |
| 9,363,863 | B2 | 6/2016 | Mercier et al. |
| 2003/0146082 | A1 | 8/2003 | Gibson et al. |
| 2008/0135041 | A1 | 6/2008 | Robison |
| 2009/0142225 | A1 | 6/2009 | Tornqvist |

FOREIGN PATENT DOCUMENTS

| | | |
|---|---|---|
| CN | 202145015 U | 2/2012 |
| CN | 204460383 U | 7/2015 |
| CN | 205586716 U | 9/2016 |
| CN | 206073200 U | 4/2017 |
| EP | 2808613 B1 | 12/2016 |
| WO | 2013160517 A1 | 10/2013 |

*Primary Examiner* — Robert A Hopkins
(74) *Attorney, Agent, or Firm* — Akerman LLP

(57) ABSTRACT

According to one embodiment, an ultraviolet light system includes an ultraviolet light source configured to be coupled inside of a ventilation hood plenum, and a light power module. The light power module includes a base configured to be coupled to an outside surface of a wall of the plenum, and further includes a light connector. The light connector is configured to extend into the inside of the plenum through the wall. The ultraviolet light source further includes a light wire positionable entirely within the plenum. The light wire has a first end configured to be coupled to the ultraviolet light source, and a second end that is configured to be coupled to the light connector.

23 Claims, 6 Drawing Sheets

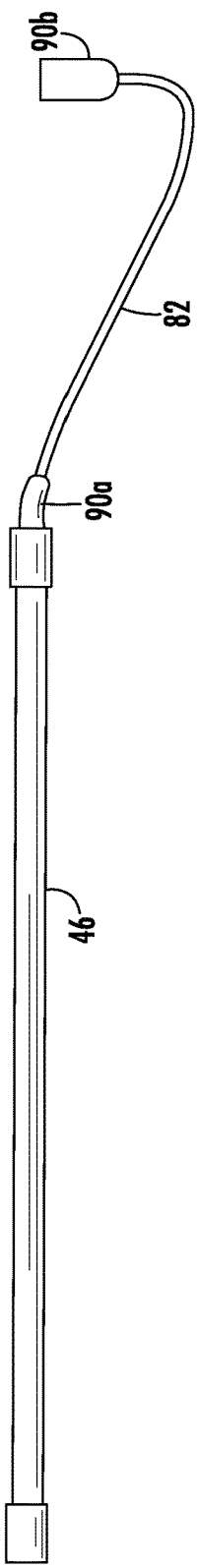

ULTRAVIOLET LIGHT SYSTEM

TECHNICAL FIELD

This disclosure relates generally to the field of ventilators and more specifically to an ultraviolet light system for a ventilator.

BACKGROUND

Cooking devices (e.g., ovens) tend to produce airborne grease, combustion products, fumes, smoke, odors, heat, and/or steam. To remove these elements, a kitchen may traditionally include a ventilator. Furthermore, some traditional ventilators may include an ultraviolet lamp that can assist in removing grease and/or odors (or other elements). These traditional ultraviolet lamps, however, may be deficient.

SUMMARY

According to one embodiment, a ventilation system includes a ventilation hood plenum coupled to a ventilation exhaust outlet, and further includes an ultraviolet light system. The ultraviolet light system includes an ultraviolet light source coupled inside of the ventilation hood plenum, and further includes a light power module. The light power module includes a base coupled to an outside surface of a wall of the ventilation hood plenum, and further includes a light connector extending out of the base. The light connector further extends into the inside of the ventilation hood plenum through the wall of the ventilation hood plenum. The ultraviolet light system further includes a light wire positioned entirely within the ventilation hood plenum. The light wire has a first end that is detachably (or undetachably) coupled to the ultraviolet light source, and further has a second end that is detachably (or undetachably) coupled to the light connector.

The light power module may further include a ballast connector extending out of the base. The ultraviolet light system may further include a ballast coupled to the ventilation system in a position outside of the ventilation hood plenum, and may further include a ballast wire positioned outside of the ventilation hood plenum. The ballast wire may have a first end that is detachably (or undetachably) coupled to the ballast, and may further have a second end that is detachably (or undetachably) coupled to the ballast connector.

The ventilation system may further include a flexible shield positioned entirely within the ventilation hood plenum. The flexible shield may enclose at least a portion of the light connector and further enclose at least a portion of the light wire. The flexible shield may be made of silicone. The flexible shield may be made of silicone, urethane, thermoplastic elastomers, rubber, synthetic rubber, fabric, glass fiber, aramid fiber, or carbon fiber.

The ventilation system may further include one or more grease baffles positioned at least partially inside of the ventilation hood plenum. Furthermore, the ultraviolet light source may be coupled inside of the ventilation hood plenum, or downstream thereof, in a location in-between the grease baffle and the ventilation exhaust outlet.

According to another embodiment, an ultraviolet light system includes an ultraviolet light source configured to be coupled inside of a ventilation hood plenum, and further includes a light power module. The light power module includes a base configured to be coupled to an outside surface of a wall of the ventilation hood plenum, and further includes a light connector extending out of the base. The light connector is configured to extend into the inside of the ventilation hood plenum through the wall of the ventilation hood plenum. The ultraviolet light source further includes a light wire positionable entirely within the ventilation hood plenum. The light wire has a first end configured to be detachably (or undetachably) coupled to the ultraviolet light source, and further has a second end that is configured to be detachably (or undetachably) coupled to the light connector.

According to another embodiment, a method includes coupling an ultraviolet light source inside of a ventilation hood plenum, and coupling a base of a light power module to an outside surface of a wall of the ventilation hood plenum. The light power module further includes a light connector extending out of the base. The light connector further extends into the inside of the ventilation hood plenum through the wall of the ventilation hood plenum. The method further includes positioning a light wire entirely within the ventilation hood plenum. The light wire has a first end that is detachably (or undetachably) coupled to the ultraviolet light source, and further has a second end that is detachably (or undetachably) coupled to the light connector.

The light power module may further include a ballast connector extending out of the base. Furthermore, the method may also include coupling a ballast to a ventilation system in a position outside of the ventilation hood plenum, coupling a first end of a ballast wire to the ballast, and coupling a second end of the ballast wire to the ballast connector. The ballast wire may be positioned entirely outside of the ventilation hood plenum.

One or more grease baffles may be positioned at least partially inside of the ventilation hood plenum, and the ventilation exhaust outlet may be coupled to the ventilation hood plenum. Furthermore, the method may further include coupling the ultraviolet light source inside of the ventilation hood plenum in a location in-between the grease baffles and the ventilation exhaust outlet.

BRIEF DESCRIPTION OF THE FIGURES

For a more complete understanding of the present disclosure and its features and advantages, reference is now made to the following description, taken in conjunction with the accompanying drawings, in which:

FIGS. 1A-1C illustrate an example ventilation system;

DETAILED DESCRIPTION

Embodiments of the present disclosure are best understood by referring to FIGS. 1A-3 of the drawings, like numerals being used for like and corresponding parts of the various drawings.

Cooking devices (e.g., ovens) tend to produce airborne grease, combustion products, fumes, smoke, odors, heat, and/or steam. To remove these elements, a kitchen may traditionally include a ventilator. Furthermore, some traditional ventilators may include an ultraviolet lamp that can assist in removing grease (or other elements)). These traditional ultraviolet lamps, however, may be deficient. For example, traditional ultraviolet lamps may require bulky cassette-type housings to secure the lamps within the ventilator and protect electronics from the environment (e.g., grease, high temperatures, etc.) of the ventilator. These bulky cassette-type housings may restrict airflow because of their large footprint. As another example, such traditional ultraviolet lamps may further require substantial custom modifications to the ventilation hood plenum of the ventilator in order for these traditional ultraviolet lamps to fit within a ventilator. These substantial modifications may be expensive and/or burdensome. Furthermore, in order to replace one or more parts of these traditional ultraviolet lamps (e.g., to replace a part, to clean a part, etc.), all or a large portion of the ultraviolet lamp must be removed (along with a large portion of the ventilator/cassette-type housing), even portions that do not need to be replaced. Contrary to such typical deficiencies, the ventilation system of FIGS. 1A-3 may provide one or more advantages.

Figure 1A:
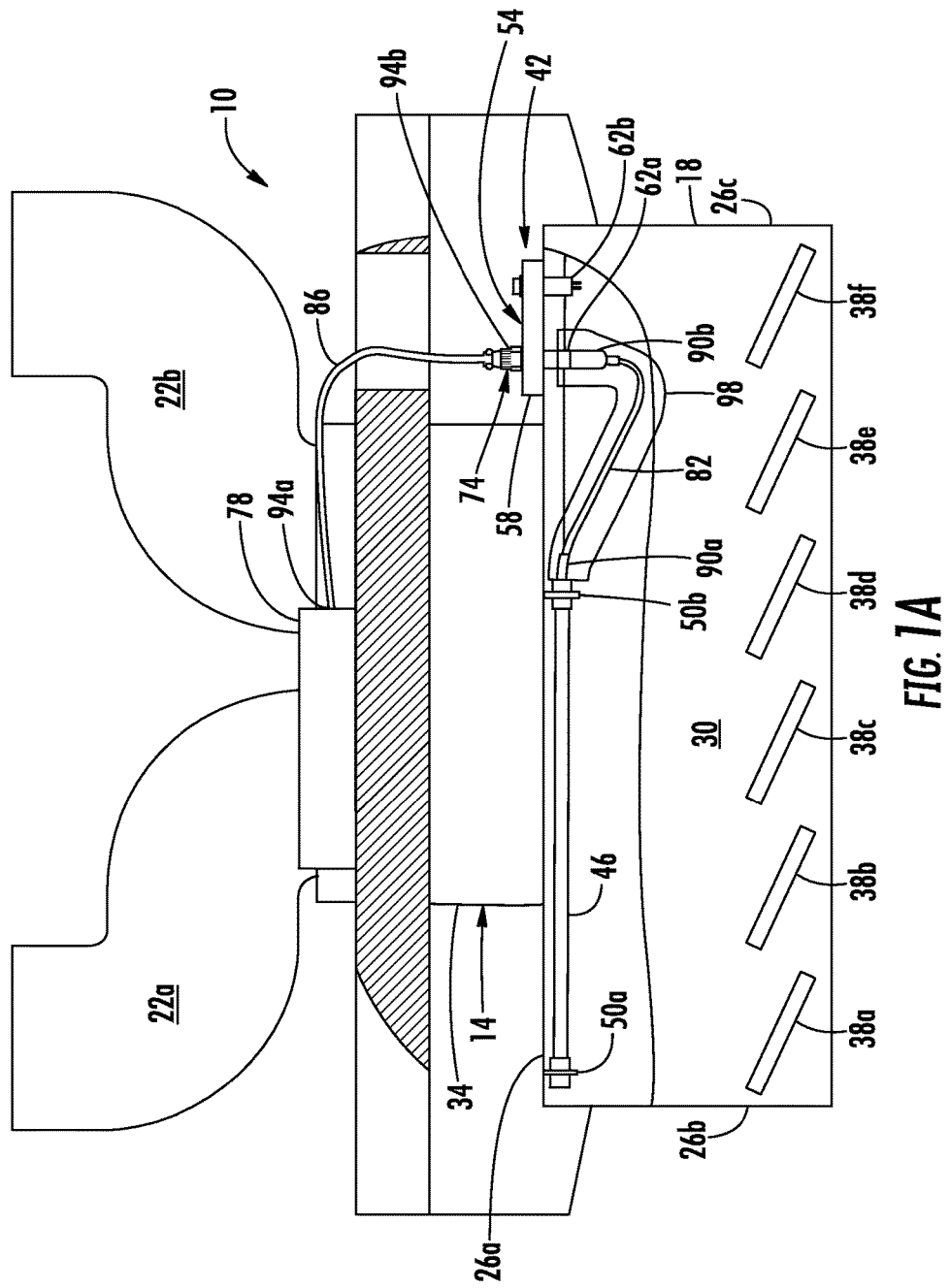
Figure 1B:
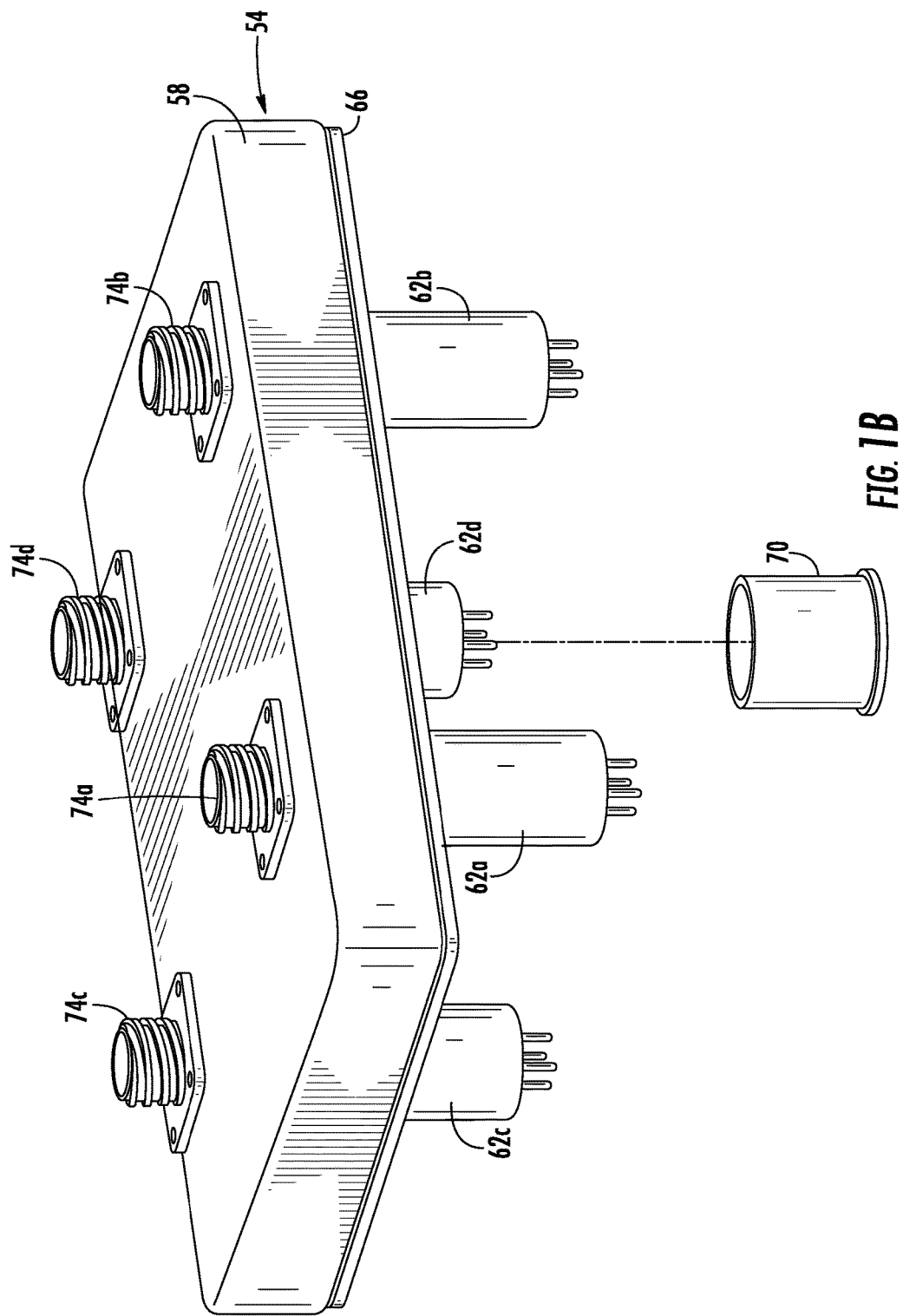

FIGS. 1A-1C illustrate an example ventilation system. In particular, FIG. 1A illustrates a cross sectional view of an example ventilation system 10 having a ventilator 14 and an ultraviolet light system 42; FIG. 1B illustrates an enlarged perspective view of an example light power module 54 of the ultraviolet light system 42; and FIG. 1C illustrates an enlarged view of an example ultraviolet light source 46 and an example light wire 82 of the ultraviolet light system 42.

The ventilation system 10 may include a ventilator 14 that may remove (e.g., via evacuation and/or filtration) airborne grease, combustion products, fumes, smoke, odors, heat, and/or steam by one or more cooking devices. The ventilator 14 is typically positioned over one or more cooking devices, such as one or more stoves, broilers, fryers, any other devices for cooking, or any combination of the preceding. To position the ventilator 14 over the cooking device(s), the ventilator 14 is typically fixed to a wall and/or suspended from the ceiling. The ventilator 14 may be used in any type of cooking environment, such as in a home kitchen, a professional kitchen, a restaurant kitchen, or any other kitchen environment.

As is illustrated, the ventilator 14 may include a ventilation hood plenum 18 coupled to one or more ventilation exhaust outlets 22. When cooking exhaust is created using the cooking device(s), the ventilator 14 may draw the cooking exhaust into the ventilator hood plenum 18, and then remove the airborne grease, combustion products, fumes, smoke, odors, heat, and/or steam. Then, the cleaned (or cleaner) cooking exhaust may be expelled from the ventilator 18 through the ventilation exhaust outlet(s) 22.

The ventilation hood plenum 18 may be a portion of the ventilator 14 that is positioned over the one or more cooking devices, so as to capture the cooking exhaust produced by the cooking devices. The ventilation hood plenum 18 may have any shape and/or size for capturing cooking exhaust. The ventilation hood plenum 18 may include one or more walls 26 that define the shape and/or size of the ventilation hood plenum 18. As illustrated, the ventilation hood plenum 18 includes five walls 26: a top wall 26a, a left side wall 26b, a right side wall 26c, a front side wall 26d (not shown), and a back side wall 26e (also not shown). In addition to defining the shape and/or size of the ventilation hood plenum 18, the inside surfaces of the walls 26 may further define an inside portion 30 of the ventilation hood plenum 18.

The ventilator 14 may further include one or more ventilation exhaust outlets 22 that may expel the cooking exhaust out of the ventilator 14 after the ventilator 14 has removed the airborne grease, combustion products, fumes, smoke, odors, heat, and/or steam. The ventilator 14 may include any number of ventilation exhaust outlets 22. As is illustrated, the ventilator 14 includes two ventilation exhaust outlets 22a and 22b.

The ventilation exhaust outlets 22 may be coupled to the ventilation hood plenum 18 in any manner. Furthermore, the ventilation exhaust outlets 22 may be directly coupled to the ventilation hood plenum 18, or indirectly coupled to the ventilation hood plenum 18. As is illustrated, the ventilation exhaust outlets 22 are indirectly coupled to the ventilation hood plenum 18 by a duct system 34 that allows air to pass from the ventilation hood plenum 18 to the ventilation exhaust outlets 22. The duct system 34 may have any shape and/or size. Furthermore, the duct system 34 may include one or more fans (not shown) that may draw cooking exhaust into the ventilation hood plenum 18, into the duct system 34, and out the ventilation exhaust outlets 22.

The ventilator 14 may further include one or more grease baffles 38 positioned at least partially within the ventilation hood plenum 18. The grease baffles 38 may provide a winding flow path that may help extract airborne grease (and other elements) from the cooking exhaust. The ventilator 14 may include any number of grease baffles 38. As is illustrated, the ventilator 14 includes six grease baffles 38: grease baffles 38a-f. Furthermore, although grease baffles 38a-f have been illustrated as six separate grease baffles 38, in some examples, each of the grease baffles 38 may be connected together to form a single multi-path grease baffle 38. The grease baffles 38 may be positioned at any location in the ventilation hood plenum 18. In some examples, one or more of the grease baffles 38 may extend at least partially outside of the inside portion 30 of the ventilation hood plenum 18. In other examples, the grease baffles 38 may be positioned entirely within the inside portion 30 of the ventilation hood plenum 18.

The ventilator 14 may further include one or more filters (not shown) that further help remove airborne grease (and other elements) from the cooking exhaust. Ventilator 14 may include any type of filter(s), and the filter(s) may be positioned in any location in the ventilator 14. For example, the filter(s) may be positioned in the inside portion 30 of ventilation hood plenum 18 in a location in-between the grease baffles 38 and the ultraviolet light source 46 (discussed below).

As is further illustrated in FIGS. 1A and 1C, the ventilation system 10 may also include an ultraviolet light system 42. The ultraviolet light system 42 may include an ultraviolet light source 46 that emits ultraviolet radiation, which may break down airborne grease in the cooking exhaust (e.g., it may break down the airborne grease into carbon dioxide and water). This may prevent the grease from sticking onto the walls 26 of the ventilation hood plenum 18 or ducting (or other surfaces of the ventilator 14), in some examples. Furthermore, the ultraviolet radiation may also assist in removing one or more odors (or other elements) from the cooking exhaust.

The ultraviolet light system 42 may be installed in either a new ventilator 14 (e.g., a ventilator 14 designed and/or built to include the ultraviolet light system 42) or a pre-existing ventilator 14 (e.g., a ventilator 14 that was not originally designed and/or built to include the ultraviolet light system 42). In some examples, the ultraviolet light system 42 may be installed in ventilators 14 that do not have a shape and/or size that is big enough to hold traditional ultraviolet systems. For example, traditional ultraviolet systems may be too big to fit into particular ventilators 14, or may require an installation of a bulky cassette-type housing that is too big to fit into (or on) particular ventilators 14. Contrary to these deficiencies, the ultraviolet light system 14 may be installed on such particular ventilators 14. Furthermore, in some examples, the ultraviolet light system 42 may be installed on ventilators 14 without requiring substantial modifications to the ventilator 14. For example, the modifications for ultraviolet light system 42 may only include creating one or more openings or penetrations (discussed below) in the ventilation hood plenum 18.

As is illustrated, the ultraviolet light system 42 may include one or more ultraviolet light sources 46. An ultraviolet light source 46 may be any device that may emit (or radiate) ultraviolet radiation. As an example, the ultraviolet light source 46 may be a lamp that emits (or radiates) ultraviolet radiation. Further example of the ultraviolet light source 46 may include a low-pressure mercury vapor discharge lamp, a low-pressure mercury vapor discharge lamp with a high output filament, a low pressure mercury vapor discharge lamp with a high output filament and having an amalgam container containing an amalgam positioned behind an electrode out of the arc path or space, any other device that may emit (or radiate) ultraviolet radiation, or any combination of the preceding. In some examples, the ultraviolet light source 42 may be a Heraeus Noblelight (part number NIL 290/154 XL). In some examples, the ultraviolet light source 42 may have an envelope (for the light source) that is made of synthetic or natural borosilica, sola-lime silica, or fused natural silica material.

The ultraviolet light source 46 may have any size, length, filament configuration, envelope materials, and/or power levels. Also, the ultraviolet light system 42 may include any number of ultraviolet light sources 46. For example, the ultraviolet light system 42 may include one ultraviolet light source 46, two ultraviolet light sources 46, three ultraviolet light sources 46, five ultraviolet light sources 46, or any other number of ultraviolet light sources 46.

The ultraviolet light source 46 may be positioned inside of the ventilation hood plenum 18. For example, the ultraviolet light source 46 may be positioned entirely within the inside portion 30 of the ventilation hood plenum 18. The ultraviolet light source 46 may be positioned at any location inside of the ventilation hood plenum 18. For example, the ultraviolet light source 46 may be positioned inside the ventilation hood plenum 18 at a location in-between the grease baffles 38 and the ventilation exhaust outlets 22. As another example, the ultraviolet light source 46 may be positioned inside the ventilation hood plenum 18 at a location in-between the grease baffles 38 and the duct system 34.

In order to position the ultraviolet light source 46 inside of the ventilation hood plenum 18, the ultraviolet light source 46 may be coupled inside of the ventilation hood plenum 18. The ultraviolet light source 46 may be coupled to any surface inside of the ventilation hood plenum 18. For example, the ultraviolet light source 46 may be coupled to an inside surface of any of the walls 26 of the ventilation hood plenum 18. As is illustrated, the ultraviolet light source 46 is coupled to the inside surface of the top wall 26a of the ventilation hood plenum 18.

The ultraviolet light source 46 may be coupled inside the ventilation hood plenum 18 in any manner. For example, the ultraviolet light source 46 may be coupled inside the ventilation hood plenum 18 using one or more lamp mounts 50. A lamp mount 50 may be any device or structure that may couple the ultraviolet light source 46 to one or more surfaces inside the ventilation hood plenum 18. As an example, the lamp mount 50 may be a clip (e.g., a sheet metal clip), an adhesive, a mount, a screw, an EMT clip, or any other device (or structure) that may couple the ultraviolet light source 46 to one or more surfaces inside the ventilation hood plenum 18.

The lamp mount 50 may provide a detachable coupling of the ultraviolet light source 46 to the inside of the ventilation hood plenum 18. This detachable coupling may couple the ultraviolet light source 46 to the inside of the ventilation hood plenum 18, and it may also allow the ultraviolet light source 46 to be uncoupled from the inside of the ventilation hood plenum 18. As such, the ultraviolet light source 46 may be removed from its coupling, so as to repair, replace, or clean the ultraviolet light source 46 when appropriate.

The ultraviolet light system 42 may further include a light power module 54 that may provide power (e.g., electrical power) to the ultraviolet light source 46. The light power module 54 may include a base 58 and one or more light connectors 62 that extend out of the base 58. The base 58 may be coupled to an outside surface of a wall 26 of the ventilation hood plenum 18. Such a coupling may allow a majority of the light power module 54 to remain outside of the ventilation hood plenum 18. As such, the majority of the light power module 54 may not be exposed to (or may have less exposure to) the airborne grease, flames, and/or heat included in the environment of the ventilator 14. This may, in some examples, allow the light power module 54 to be installed in a ventilator 14 without enclosing the light power module 54 within a bulky cassette-type housing that may have traditionally been used to protect electronics from airborne grease, flames, and/or heat.

Such a coupling may also allow the light power module 54 to be more easily installed on a ventilator 14. For example, because the majority the light power module 54 remains outside of the ventilation hood plenum 18 (e.g., outside of the inside portion 30 of the ventilation hood plenum 18), the shape and/or size of the inside portion 30 of the ventilation hood plenum 18 does not have to be built (and/or modified) to be able to hold or enclose the shape and/or size of a majority of the light power module 54. Instead, the inside portion 30 of the ventilation hood plenum 18 may only need to be able to hold (or otherwise enclose) the light connectors 62 that penetrate through the wall(s) 26 of the ventilation hood plenum 18 into the inside portion 30 of the ventilation hood plenum 18.

The base 58 may be coupled to an outside surface of any of the walls 26 of the ventilation hood plenum 18. As is illustrated in FIG. 1A, the base 58 may be coupled to an outside surface of the top wall 26a of the ventilation hood plenum 18. In some examples, the base 58 may be coupled to an outside surface of a wall 26 of the ventilation hood plenum 18 in any location (or surface) in-between the grease baffles 38 and the ventilation exhaust outlet 22 (or in-between the grease baffles 38 and the duct system 34). The base 58 may be coupled to an outside surface of a wall 26 in any manner. As an example, the base 58 may be coupled to an outside surface of the wall 26 using one or more screws, bolts, nails, clips, adhesive, or any other coupling device that may couple the base 58 to the outside surface of the wall 26.

Although the base 58 may be coupled to an outside surface of a wall 26 of the ventilation hood plenum 18, in some examples, a sealing gasket 66 (shown in FIG. 1B) may be positioned in-between the base 58 and the outside surface of the wall 26. The sealing gasket 66 may provide a seal between the base 58 and the outside surface of the wall 26. This may prevent gas exhaust, airborne grease, flames, heat, and/or other elements from passing out of the inside portion 30 of the ventilation hood plenum 18 to the exterior through one or more holes or openings in the ventilation hood plenum 18 (discussed below). It may also cause the ventilation hood plenum 18 to be liquid-tight, as required by American National Standards Institute (ANSI)/Underwriters Laboratories (UL).

The light power module 54 may further include one or more light connectors 62 that extend out of the base 58. A light connector 62 may be any portion of the light power module 54 that may provide a power connection between the light power module 54 and the ultraviolet light source 46. For example, as is illustrated, the light connector 62 may be a fitting onto which (or into which) a light wire 82 (discussed below) may be connected so that power may be provided to the ultraviolet light source 46.

In addition to extending out of the base 58, a light connector 62 may further extend into the inside portion 30 of the ventilation hood plenum 18 through a wall 26 of the ventilation hood plenum 18. That is, the light connector 62 may penetrate through the wall 26, allowing it to extend in the inside portion 30 of the ventilation hood plenum. In order for the light connector 62 to extend into the inside portion 30 of the ventilation hood plenum 18, the wall 26 of the ventilation hood plenum 18 may include (or may be modified to include) one or more openings. Each of these openings may have a shape and/or size that allows one or more of the light connectors 62 to fit through the opening in order to extend into the inside portion 30 of the ventilation hood plenum 18 through the wall 26.

The light connector 62 may extend through any wall(s) 26 (or other surface) of the ventilation hood plenum 18 in order to extend into the inside portion 30 of the ventilation hood plenum 18. For example, the light connector 62 may extend through the top wall 26a, the left side wall 26b, the right side wall 26c, the front side wall 26d, the back side wall 26e, any other surface of the ventilation hood plenum 18, or any combination of the preceding. In some examples, the light connector 62 may extend through a wall 26 in a location that is in-between the grease baffles 38 and the ventilation exhaust outlets 22. In further examples, the light connector 62 may extend through a wall 26 in a location that is in-between the grease baffles 38 and the duct system 34.

The light connector 62 (or a portion of the light connector 62) may be the only portion of the light power module 54 that penetrates the ventilation hood plenum 18 and extends into the inside portion 30 of the ventilation hood plenum 18. In some examples, the light connector 62 (or a portion light connector 62) may be the only power supply element that penetrates the ventilation hood plenum 18 and extends into the inside portion 30 of the ventilation hood plenum 18.

By extending into the inside portion 30 of the ventilation hood plenum 18, the light connector 62 may provide a power connection within the inside portion 30 of the ventilation hood plenum 18, even though the majority of the light power module 54 may be positioned outside the inside portion 30. This may allow power to be provided to the ultraviolet light source 46 without the majority of the light power module 54 needing to be positioned within the inside portion 30 of the ventilation hood plenum 18 (where it may be exposed to grease, heat, and/or fire), for example.

In some examples, the minimal penetration provided by the light connector 62 extending into the inside portion 30 of the ventilation hood plenum 18 may assist in preserving the ventilation hood plenum 18's ability to contain heat and/or flames according to one or more regular regulatory requirements. For example, the light connector 62 (and its penetration into the inside portion 30 of the ventilation hood plenum 18) may comply with applicable Underwriters Laboratories (UL) and National Fire Protection Association (NFPA) regulatory requirements.

The light connector 62 may have any shape and/or size that allows it to extend into the inside portion 30 of the ventilation hood plenum 18 so as to provide a power connection for the ultraviolet light source 46. The light connector 62 may be made of any material that may at least partially resist degradation from fire, heat, grease, and/or other elements inside the ventilator 14. For example, the light connector 62 may be made of a metallic material, such as steel, stainless steel, aluminum, copper, brass alloys, or any combination of the preceding. As another example, the light connector 62 may be made of (or be coated with) a material that may provide electrical insulation in addition to at least partially resisting degradation (e.g., from fire, heat, etc.), such as, for example, ceramic, phenolic, polyetherimide, polyether ether ketone, polyester, polyamide, and/or glass.

Furthermore, all or a portion of the light connector 62 may include a coating (e.g., anodized coating, passivized coating, plated coating, and/or painted coating). Such coatings may further resist degradation (e.g., from fire, heat, etc.), thereby increasing the ability of the light connector 62 to withstand the environment of inside the ventilation hood plenum 18.

The light power module 54 may include any number of light connectors 62. For example, the light power module 54 may include one light connector 62, two light connectors 62, three light connectors 62, four light connectors 62, or any other number of light connectors 62. As is illustrated in FIG. 1B, the light power module 54 includes four light connectors 62: light connectors 62a-d. In some examples, the light power module 54 may include the same number of light connectors 62 as ultraviolet light sources 46. For example, if the ventilation system 10 includes four ultraviolet light sources 46 coupled within the inside portion 30 of the ventilation hood plenum 18, the light power module 54 may include four light connectors 62 (e.g., a light connector 62 for each of the ultraviolet light sources 46). In other examples, the light power module 54 may include more light connectors 62 than ultraviolet light sources 46. In such examples, unused light connectors 62 may be capped off using, for example, a protective cap 70 that may protect the unused light connector 62. In other examples, the light power module 54 may include less light connectors 62 than ultraviolet light sources 46. In such examples, a light connector 62 may provide a power connection for more than one ultraviolet light source 46.

The light power module 54 may further include one or more power connectors 74 that extend out of the base 58. A power connector 74 may be any portion of the light power module 54 that may provide a power connection between a power source 78 and the light power module 54. The power source 78 may be a source that provides power (e.g., electrical power) for an ultraviolet light source 46. As an example, the power source 78 may be an electrical outlet that connects to electrical wires within a structure in which the ventilator system 10 is set up. As is illustrated, the power source 78 may be a ballast (discussed below). In examples where the power source 78 is a ballast, the power connectors 74 may be referred to as ballast connectors 74.

The power connector 74 may have any shape and/or size that allows it to extend out of the base 58 so as to provide a power connection between the power source 78 and the light power module 54. The power connector 74 may be made of any material that may allow it to operate as a power connection. For example, the power connector 74 may be made of a metallic material, such as steel, stainless steel, aluminum, copper, brass alloys, or any combination of the preceding. As another example, the power connector 74 may be made of (or be coated with) a material that may provide electrical insulation in addition to allowing the power connector 74 to operate as a power connection, such as, for example, ceramic, phenolic, polyetherimide, polyether ether ketone, polyester, polyamide, and/or glass.

The light power module 54 may include any number of power connectors 74. For example, the light power module 54 may include one power connector 74, two power connectors 74, three power connectors 74, four power connectors 74, or any other number of power connectors 74. As is illustrated in FIG. 1B, the light power module 54 includes four power connectors 74: power connectors 74a-d. In some examples, the light power module 54 may include the same number of power connectors 74 as light connectors 62. For example, if the light power module 54 includes four light connectors 74, the light power module 54 may also include four power connectors 74 (e.g., a power connector 74 for each of the light connectors 62). In such examples, each power connector 74 may supply power directly (or indirectly) to a separate light connector 62. In other examples, the light power module 54 may include more power connectors 74 than light connectors 62. In such examples, unused power connectors 74 may be capped off using, for example, a protective cap that may protect the unused power connector 74. The protective cap may be similar to protective cap 70. In other examples, the light power module 54 may include less power connectors 74 than light connectors 62. In such examples, a power connector 74 may supply power to more than one light connector 62.

As is discussed above, power may be provided to the light power module 54 by a power source 78. This power source 78 may be any source that may provide power for an ultraviolet light source 46. For example, the power source 78 may be an electrical outlet. According to the illustrated embodiment, the power source 78 is a ballast. The ballast 78 may be any device that may limit an amount of current in an electrical circuit. By limiting the amount of current, the ballast 78 may prevent the current from rising to a level that may destroy and/or negatively affect the light power module 54 and/or the ultraviolet light source 46. In some examples, the ballast 78 may be an intermediary device located between another power source (such as an electrical line or electrical outlet) and the light power module 54. As such, the ballast 78 may protect the light power module 54 and/or the ultraviolet light source 46 from an electrical current that is too high. Furthermore, the ballast 78 may convert electrical voltage and/or frequency to levels required by the ultraviolet light source 46 for proper operation.

As is illustrated, the ballast 78 may be coupled to the ventilation system 10 in a location that is outside of the inside portion 30 of the ventilation hood plenum 18. As such, the ballast 78 may not be located within the inside portion 30 of the ventilation hood plenum 18. The ballast 78 may be coupled to the ventilation system 10 in any location that is located outside of the inside portion 30 of the ventilation hood plenum 18. For example, the ballast 78 may be coupled to an outside surface of a wall 26 of the ventilation hood plenum 18, an outside surface of the duct system 34, an outside surface of the ventilation exhaust outlets 22, a ceiling of the structure in which the ventilation system 10 is installed, or any other surface of the structure in which the ventilation system 10 is installed.

The ultraviolet light system 42 may further include one or more light wires 82 and one or more power wires 86. A light wire 82 may be any power connection wire that can connect to both the light connector 62 and the ultraviolet light system 46 in order to provide power to the ultraviolet light system 46.

As is illustrated, the light wire 82 may include a first end 90a and a second end 90b. The first end 90a may be coupled to the ultraviolet light source 46. The first end 90a may be coupled to the ultraviolet light source 46 in any manner. For example, the first end 90a may be undetachably coupled to the ultraviolet light source 46. Such an undetachable coupling may refer to a permanent coupling that may only be uncoupled as a result of breaking the first end 90a off (or otherwise permanently severing the connection with) the ultraviolet light source 46. As an example of this undetachable coupling, the first end 90a (and/or the wire or connectors within the first end 90a) may be directly connected to internal filament leads (or wires) of the ultraviolet light source 46. As a result of the undetachable coupling, the light wire 82 may be a permanent attachment to the ultraviolet light source 46. Therefore, if the ultraviolet light source 46 is replaced, the replacement ultraviolet light source 46 may already have the light wire 82 undetachably coupled to it. This may prevent a user from having to purchase or provide a separate light wire 82.

In another example, the first end 90a may be detachably coupled to the ultraviolet light source 46. The detachable coupling may refer to a coupling that may be detached and reattached at any time without breaking (or otherwise destroying) the light wire 82 and/or the ultraviolet light source 46. As an example of the detachable coupling, the first end 90a may be (or have) a male connector piece that is plugged into or is screwed into (or on) a corresponding female connector piece in the ultraviolet light source 46. Alternatively, the first end 90a may be (or have) a female connector piece that is plugged into or screwed into (or on) a corresponding male connector piece in the ultraviolet light source 46. In such examples, coupling the detachable first end 90a to the ultraviolet light source 46 may cause an indirect connection between the first end 90a and internal filament leads (or wires) of the ultraviolet light source 46.

As a result of the detachable coupling, if the ultraviolet light source 46 is replaced (or removed for cleaning), the replacement ultraviolet light source 46 (or cleaned ultraviolet light source 46) may be plugged into the same exact light wire 82 as the prior ultraviolet light source 46. Furthermore, if the light wire 82 is replaced (e.g., if it is broken), it may be replaced without also replacing the ultraviolet light source 46. Also, if the light wire 82 is removed for cleaning, it may be removed (and put back) without also removing (and putting back) the ultraviolet light source 46.

As is also illustrated, the light wire 82 may further include the second end 90b. The second end 90b may be coupled to the light connector 62. The second end 90b may be coupled to the light connector 62 in any manner. For example, the second end 90b may be undetachably coupled or detachably coupled to the light connector 62. Examples of these undetachable couplings and detachable couplings are discussed above with regard to the first end 90a. The detachable coupling may, in some examples, allow the light wire 82 to be replaced (e.g., if it is broken) or removed for cleaning, without having to replace the light power module 54 and/or without having to also remove the light power module 54 from its coupling to the ventilation hood plenum 18.

The light wire 82 may be positioned entirely within the inside portion 30 of the ventilation hood plenum 18. In such examples, no portion of the light wire 82 may extend outside of the inside portion 30 of the ventilation hood plenum 18. Such positioning may prevent the light wire 82 from needing to penetrate (or otherwise pass through) a wall 26 of the ventilation hood plenum 18. As such, the light wire 82 may be easier to install and/or replace, because the light wire 82 may not need to be routed through one or more openings in the wall 26 of the ventilation hood plenum 18. Furthermore, the openings in the wall 26 may be easier to seal (e.g., to prevent gas exhaust from escaping) because a possible movable light wire 82 may not extend through the openings (and/or shift within the openings).

In order to be positioned entirely within the inside portion 30 of the ventilation hood plenum 18, the light wire 82 may be coated or sheathed with one or more materials that may protect the light wire 82 from degradation (e.g., from fire, heat, etc.), and that may further provide electrical insulation. For example, the light wire 82 may be coated with ceramic, phenolic, polyetherimide, polyether ether ketone, polyester, polyamide, and/or glass. This coating or sheathing may provide a protective jacket over a bare light wire 82.

The light wire 82 may have any shape and/or size that allows it to be positioned entirely within the inside portion 30 of the ventilation hood plenum 18. Furthermore, the ultraviolet light system 42 may include any number of light wires 82. For example, the ultraviolet light system 42 may include one light wire 82, two light wires 82, three light wires 82, four light wires 82, or any other number of light wires 82. In some examples, the ultraviolet light system 42 may include the same number of light wires 82 as ultraviolet light sources 46. For example, if the ultraviolet light system 42 includes four ultraviolet light sources 46, it may also include four light wires 82 (e.g., each light wire 82 may provide power to a separate ultraviolet light source 46). In some examples, the ultraviolet light system 42 may include fewer light wires 82 than ultraviolet light sources 46. In such examples, a single light wire 82 may provide power to multiple ultraviolet light sources 46.

Although the light wire 82 of FIGS. 1A and 1C is illustrated as a single unbroken light wire 82 that extends from the light connector 62 to the ultraviolet light source 46, in some examples, the light wire 82 may be made up of two or more individual light wires 82. In such an example, these individual light wires 82 may be connected together (into a single unbroken strand) in order to extend from the light connector 62 to the ultraviolet light source 46.

The ultraviolet light system 42 may also include one or more power wires 86. A power wire 86 may be any power connection wire that can connect to both the power source 78 and the power connector 74 in order to provide power to the light power module 54 (and eventually the ultraviolet light source 46, as is explained above). Where the power source 78 is a ballast, the power wire 86 may be referred to as a ballast wire 86.

As is illustrated, the power wire 86 may include a first end 94a and a second end 94b. The first end 94a may be coupled to the power source 78. The first end 94a may be coupled to the power source 78 in any manner. For example, the first end 94a may be undetachably coupled or detachably coupled to the power source 78. Examples of these undetachable couplings and detachable couplings are discussed above with regard to the first end 90a.

As is also illustrated, the power wire 86 may further include the second end 94b. The second end 94b may be coupled to the power connector 74. The second end 94b may be coupled to the power connector 74 in any manner. For example, the second end 94b may be undetachably coupled or detachably coupled to the power connector 74. Examples of these undetachable couplings and detachable couplings are discussed above with regard to the first end 90a.

The power wire 86 may be positioned outside of the inside portion 30 of the ventilation hood plenum 18. For example, no portion of the power wire 86 may extend into the inside portion 30 of the ventilation hood plenum 18. Such positioning may prevent the power wire 86 from needing to be protected from the environment (e.g., fire, heat, etc.) in the ventilation hood plenum 18.

The power wire 86 may have any shape and/or size. Furthermore, the ultraviolet light system 42 may include any number of power wires 86. For example the ultraviolet light system 42 may include one power wire 86, two power wires 86, three power wires 86, four power wires 86, or any other number of power wires 86. In some examples, the ultraviolet light system 42 may include the same number of power wires 86 as ultraviolet light sources 46. For example, if the ultraviolet light system 42 includes four ultraviolet light sources 46, it may also include four power wires 86 (e.g., each power wire 86 may provide power for a separate ultraviolet light source 46). In some examples, the ultraviolet light system 42 may include fewer power wires 86 than ultraviolet light sources 46. In such examples, a single power wire 86 may provide power for multiple ultraviolet light sources 46.

Although the power wire 86 of FIG. 1A is illustrated as a single unbroken power wire 86 that extends from the power source 78 to the power connector 74, in some examples, the power wire 86 may be made up of two or more individual power wires 86. In such an example, these individual power wires 86 may be connected together (into a single unbroken strand) in order to extend from the power source 78 to the power connector 74.

The ultraviolet light system 42 may further include a shield 98. The shield 98 may be any device (or structure) that may shield all or a portion of the light connector 62 and/or all or a portion of the light wire 82. This shielding may at least partially resist degradation of the light connector 62 and/or light wire 82 from fire, heat, grease, and/or other elements inside the ventilator 14. The shield 98 may be a sleeve, boot, or other enclosure that is made from a material that is resistant to fire, heat, grease, and/or other elements inside the ventilator 14. In such examples, the shield 98 may be an additional layer of protection beyond the protection provided by the coating, sheathing, or protective jacket already included on the light wire 82. That is, the light wire 82 may include its own protective coating/jacket, and the shield 98 may be an additional layer (or layers) of protection positioned over the light wire 82 (and/or over the light connector 62).

The shield 98 may enclose all or a portion of the light connector 62, so as to shield the light connector 62. Furthermore, the shield 98 may enclose all or a portion of the light wire 82, so as to shield the light wire 82. As a result of this enclosure and shielding, the light wire 82 (and a portion of the light connector 62) may be positioned entirely within the inside portion 30 of the ventilation hood plenum 18, without being destroyed or substantially negatively affected by the environment inside of the ventilation hood plenum 18. For example, the shield 98 may provide additional protection to the light wire 82 and light connector 62, allowing them to remain inside of the ventilation hood plenum 18 for longer periods of time without substantial damage and/or without a need for constant cleaning. In some examples, the shield 98 may allow the light wire 82 and light connector 62 to be positioned within the inside portion 30 of the ventilation hood plenum 18 in a location that is in-between the grease baffles 38 and ventilation exhaust outlets 22 (or in-between the grease baffles 38 and the duct system 34).

To shield the light connector 62 and/or the light wire 82, the shield 98 may be positioned entirely within the inside portion 30 of the ventilation hood plenum 18. Furthermore, when positioned entirely within the inside portion 30 of the ventilation hood plenum 18, the shield 98 may be coupled to an inside surface of one or more walls 26 of the ventilation hood plenum 18, to the light connector 62, to the light wire 82, or any combination of the preceding. This coupling may be performed in any manner. For example, this coupling may be performed using clips, bolts, adhesive, by wrapping the shield 98 around the light connector 62 and/or the light wire 82, or any combination of the preceding.

As a result of shielding the light connector 62 and/or the light wire 82, in some examples, the shield 98 may need to be removed from its coupling prior to (or at the same time as) the light wire 82 being removed (e.g., for replacement or cleaning) and/or prior to (or at the same time as) the light power module 54 being removed (e.g., for replacement or cleaning).

The shield 98 may be a flexible shield. This flexibility may allow the shield 98 to conform to the shape of the light wire 82 (which may also be flexible, as is illustrated in FIG. 1A). By being flexible, the shield 98 may take up less space inside of the ventilation hood plenum 18. Thus, the shield 98 may be installed in a pre-existing ventilation hood plenum 18 without having to modify the shape and/or size of the ventilation hood plenum 18.

The shield 98 may be made of any material that is both flexible and that is also resistant to fire, heat, grease, and/or other elements inside the ventilator 14. For example the shield 98 may be made of silicone, urethane, thermoplastic elastomers, rubber, synthetic rubber, fabric, glass fiber, aramid fiber, carbon fiber, or any combination of the preceding. As is illustrated, the shield 98 is a molded silicone sleeve.

As is discussed above, the shield 98 may provide multiple layers of protection to the light wire 82 and/or light connector 62. The shield 98 may provide any number of layers of protection. For example, the shield 98 may provide one layer of protection, two layers of protection, three layers of protection, or any other number of layers of protection. Each layer of protection may be provided by the same shield 98 (e.g., a shield with multiple layers and/or multiple material types). Alternatively, each layer of protection may be provided a different shield 98 (e.g., a first shield 98 providing the first layer, a second shield 98 providing the second layer, etc.). Furthermore, different material types may be used to provide each different layer of protection.

Furthermore, in some examples, the shield 98 may replace (or be a substitute) for the coating, shielding, or protective jacket (discussed above) of the light wire 82. For example, the light wire 82 may be a bare wire that is enclosed by the shield 98. In such an example, the shield 98 may provide more protection than a typical protective jacket for a wire. To enclose the light wire 82, the shield 98 may be an overmold (or two or more layers of an overmold) that is created over the light wire 82 and the light connector 62. This overmold may be removable, so as to allow the light wire 82 to be uncoupled from the light connector 62 and/or the ultraviolet light source 46. In some examples, the overmold may not be removable when the light wire 82 is undetachably coupled to the light connector 62 and/or the ultraviolet light source 46.

Modifications, additions, combinations, or omissions may be made to the ventilation system 10 of FIGS. 1A-1C without departing from the scope of the disclosure. For example, the ventilation system 10 may not include one or more of the features discussed above with regard to FIGS. 1A-1C. As an example, the light source system 42 may not include a shield 98.

As another example, although the ultraviolet light source 46 is described above as being positioned inside of the ventilation hood plenum 18, in some examples, the ultraviolet light source 46 may be positioned in any location in-between a cooktop and the duct system 34. Thus, the ultraviolet light source 46 may be positioned outside of the ventilation hood plenum 18 (e.g., in-between the grease baffles 38 and the cooktop). In such examples, the ultraviolet light source 46 may be encased to protect users from exposure to ultraviolet light. Furthermore, in such examples, the light wire 82 may extend out of the ventilation hood plenum 18 to provide power to the ultraviolet light source 46.

Figure 2A:
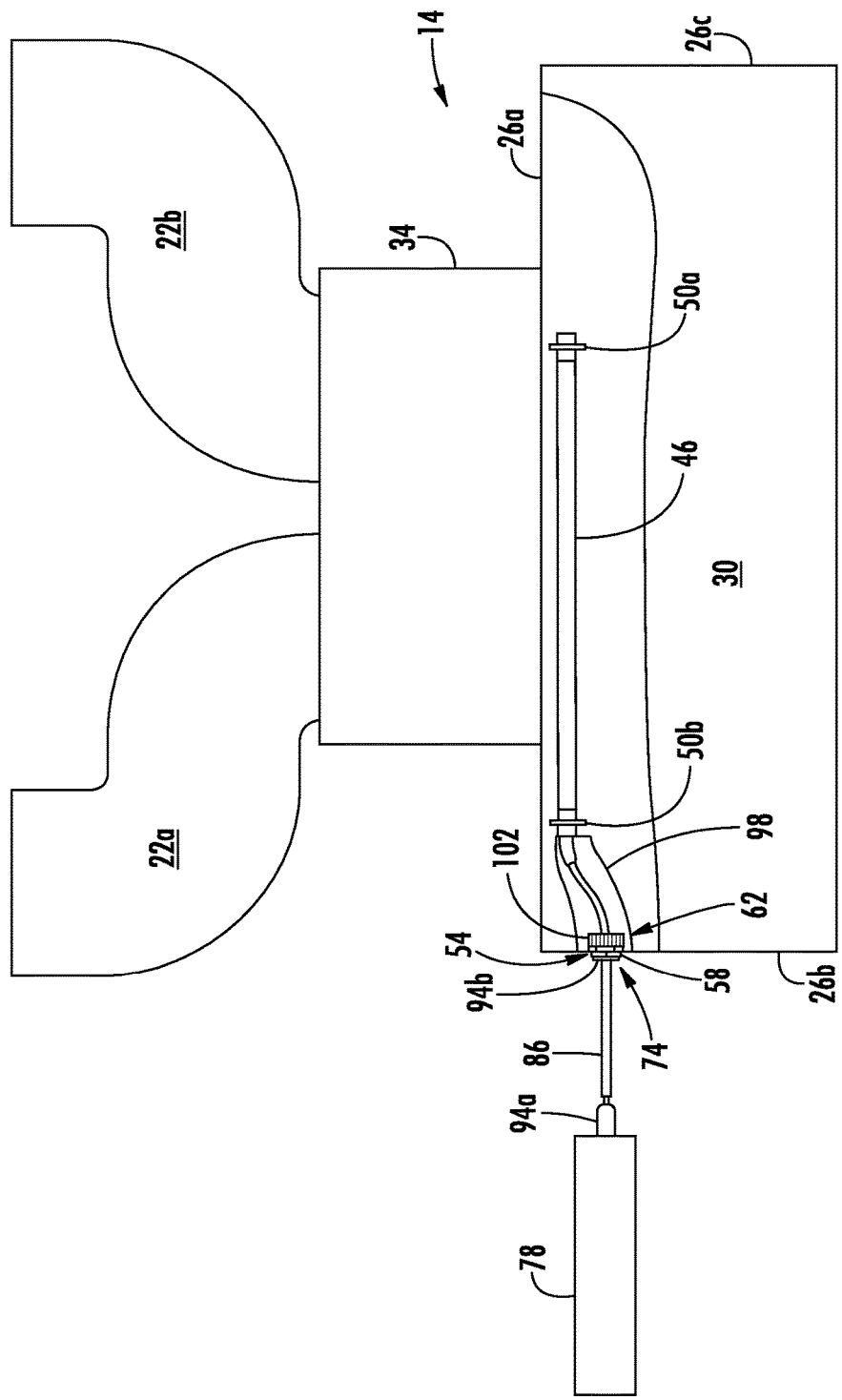
FIGS. 2A-2B illustrate another example ventilation system.
Figure 2B:
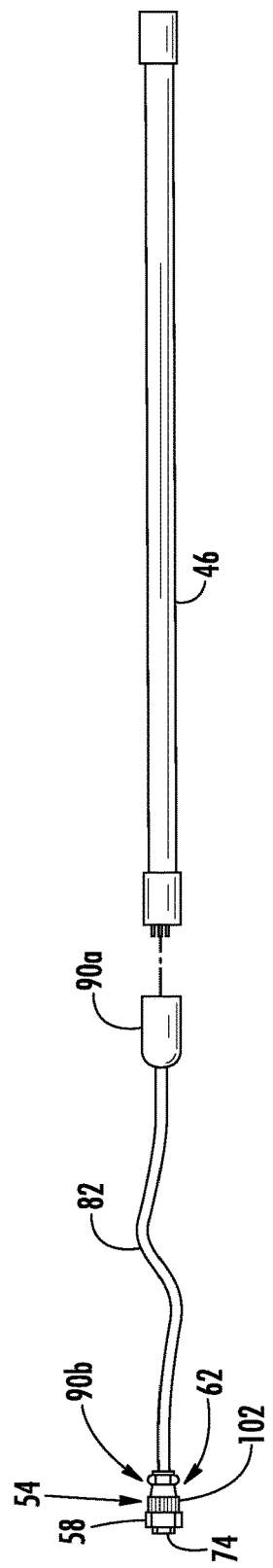

FIGS. 2A-2B illustrate another example ventilation system. In particular, FIG. 2A illustrates a cross sectional view of another example ventilation system 10 having a ventilator 14 and an ultraviolet light system 42; and FIG. 1B illustrates an enlarged perspective view of another example light power module 54, another example ultraviolet light source 46, and another example light wire 82 of the ultraviolet light system 42.

As is illustrated, the ventilation system 10 of FIGS. 2A-2B may be substantially similar to the ventilation system 10 of FIGS. 1A-1C. However, the ventilation system 10 of FIGS. 2A-2B may have a different light power module 54 than that in the ventilation system 10 of FIGS. 1A-1C.

According to the illustrated embodiment, the ventilation system 10 of FIGS. 2A-2B may include a light power module 54 that may be a sealed conduit fitting. The sealed conduit fitting 54 may include a base 58 that may be coupled to an outside surface of a wall 26 of the ventilation hood plenum 18. The base 58 may be coupled to an outside surface of any of the walls 26 of the ventilation hood plenum 18. For example, as is illustrated, the base 58 may be coupled to an outside surface of the left side wall 26b of the ventilation hood plenum 18.

The sealed conduit fitting 54 may further include a single light connector 62 that extends out of the base 58. This light connector 62 may further extend into the inside portion 30 of the ventilation hood plenum 18 through a wall 26 of the ventilation hood plenum 18. The light connector 62 may be substantially similar to the light connector 62 of FIGS. 1A-1C. The sealed conduit fitting 54 may further include a single power connector 74 that extends out of the base 58. The power connector 74 may be substantially similar to the power connector 74 of FIGS. 1A-1C.

In order to connect the sealed conduit fitting 54 to the ultraviolet light source 46, the ventilation system 10 may further include a light wire 82 that is undetachably coupled or detachably coupled to both the light connector 62 and the ultraviolet light source 46. The light wire 82 may be substantially similar to the light wire 82 of FIGS. 1A-1C. Furthermore, in order to connect the sealed conduit fitting 54 to the power source 78, the ventilation system 10 may also include a power wire 86 that is undetachably coupled or detachably coupled to both the power source 78 and the power connector 74. The power wire 86 may be substantially similar to the power wire 86 of FIGS. 1A-1C. Additional elements of the ventilation system 10 of 2A-2B not expressly discussed in this section may be substantially similar to the corresponding elements of the ventilation system 10 of FIGS. 1A-1C.

In order to couple the sealed conduit fitting 54 to the ventilation hood plenum 18, the base 58 may be positioned against an outside surface of a wall 26 of the ventilation hood plenum 18. In doing so, the light connector 62 may also be positioned or inserted through an opening in the wall 26 of the ventilation hood plenum 18, allowing the light connector 62 to extend into the inside portion 30 of the ventilation hood plenum 18. Furthermore, a nut 102 (or other connector) may be inserted around the light connector 62 and screwed (or otherwise positioned) up against the inside surface of the wall 26 of the ventilation hood plenum 18. This positioning of the nut 102 may couple the sealed conduit fitting 54 to the ventilation hood plenum 18. Furthermore, one or more sealants may be added to (or around) the sealed conduit fitting 54, so as to prevent gas exhaust, airborne grease, flames, heat, and/or other elements from passing out of the inside portion 30 of the ventilation hood plenum 18 to the exterior through the opening.

Modifications, additions, combinations, or omissions may be made to the ventilation system 10 of FIGS. 2A-2B without departing from the scope of the disclosure. For example, the orientation of the sealed conduit fitting 54 may be reversed. In such an example, the base 58 may be positioned against an inside surface of a wall 26 of the ventilation hood plenum 18. In doing so, the power connector 74 may be positioned or inserted through an opening in the wall 26 of the ventilation hood plenum 18, allowing the power connector 74 to extend out of the ventilation hood plenum 18. Furthermore, a nut 102 (or other connector) may be inserted around the power connector 74 and screwed (or otherwise positioned) up against the outside surface of the wall 26 of the ventilation hood plenum 18. This positioning of the nut 102 may couple the sealed conduit fitting 54 to the ventilation hood plenum 18.

As another example, although the sealed conduit fitting 54 is described above as being the light power module 54, in some examples, it may not be the light power module 54. Instead, it may be a standard sealed conduit fitting that provides a sealed opening through the ventilation hood plenum 18. In such examples, the light wire 82 (or the light wire 82 and the flexible shield 98) may extend entirely through the sealed conduit fitting. This may allow the light wire 82 (or the light wire 82 and the flexible shield 98) to extend outside of the ventilation hood plenum 18 (in addition to also extending inside of the ventilation hood plenum 18 to couple to the ultraviolet light source 46).

On the outside of the ventilation hood plenum 18, the light wire 82 (or the light wire 82 and the flexible shield 98) may be coupled to the light connector 62 of the light power module 54 (which is also positioned outside of the ventilation hood plenum 18). Alternatively, on the outside of the ventilation hood plenum 18, the light wire 82 (or the light wire 82 and the flexible shield 98) may be coupled directly to power source 78 (e.g., a ballast). In such an example, a light power module 54 may not be utilized. Furthermore, all of the couplings may be detachable couplings or undetachable couplings, as is discussed above.

Additionally, more than one light wire 82 (or light wire 82 and flexible shield 98) may extend through the sealed conduit fitting, so as to couple to ultraviolet light source(s) 46 and so as to further couple to the light power module 54 (or the power source 78). In such examples, any number of light wires 82 (or light wires 82 and flexible shields 98) may extend through the sealed conduit fitting.

Figure 3:
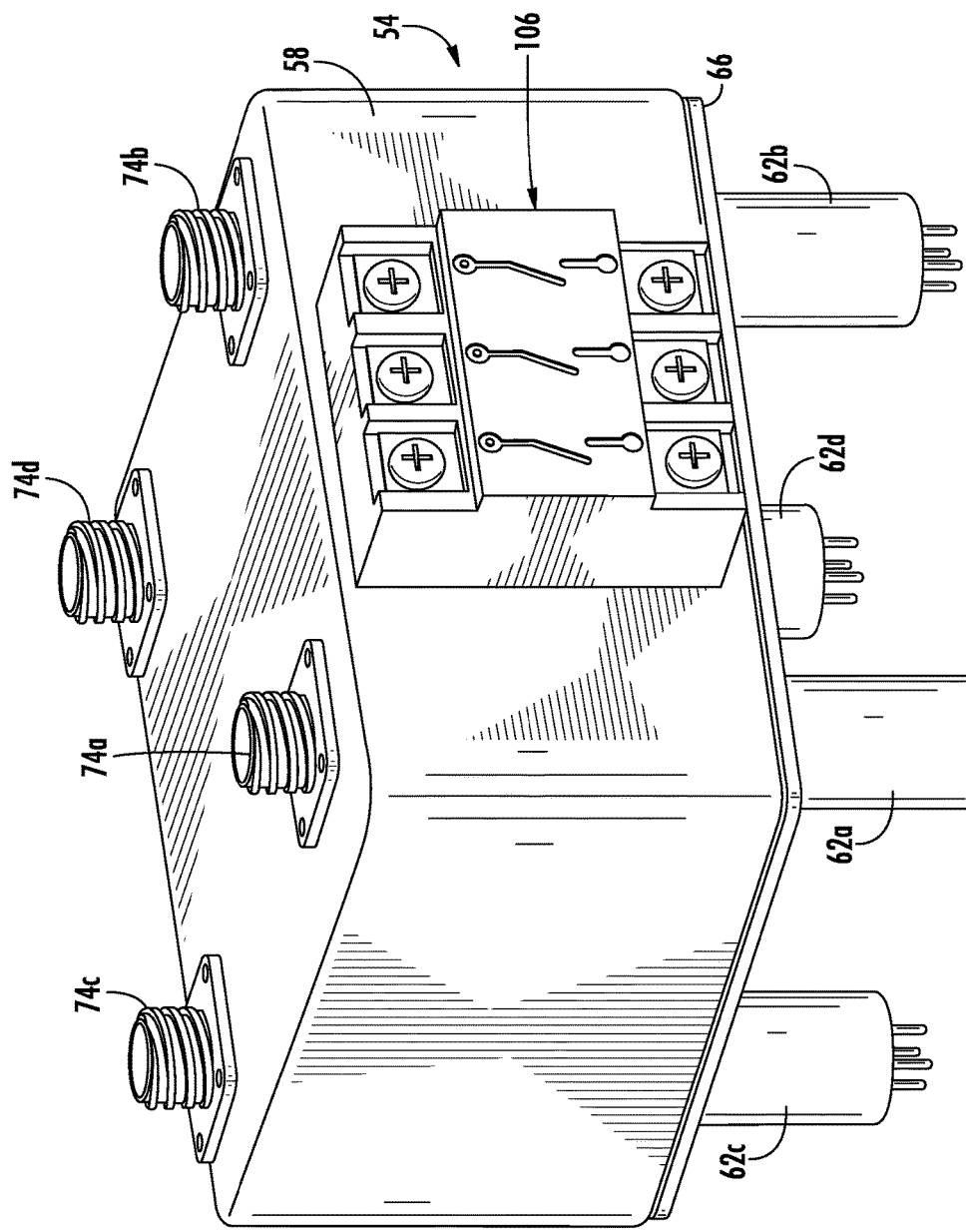
FIG. 3 illustrates another example of a light power module.

FIG. 3 illustrates another example of a light power module. The light power module 54 of FIG. 3 may be substantially similar to the light power module 54 of FIGS. 1A-1C; however, the light power module 54 of FIG. 3 may further include one or more safety interlock switches 106.

A safety interlock switch 106 may be any device that may make or break an electrical connection. As is illustrated, the safety interlock switch 106 may provide a connection (not shown) between one or more of the light connectors 62 and one or more of the power connectors 74. In addition to providing this connection, the safety interlock switch 106 may also break the connection between one or more of the light connectors 62 and one or more of the power connectors 74. This may prevent power from being provided to a light connector 62 from a power connector 74, which may subsequently prevent power from being provided to an ultraviolet light source 46. Thus, when the safety interlock switch 106 breaks the electrical connection, the ultraviolet light source 46 may stop emitting ultraviolet radiation. The safety interlock switch 106 may be specifically designed for high voltage high frequency power switching.

The safety power switch 106 may break the electrical connection in response to a signal received from a sensor. For example, the safety power switch 106 may break the electrical connection in response to a signal received from a filter switch sensor. This filter switch sensor may determine whether a grease baffle 38 or a filter has been dislodged from the ventilation hood plenum 18. If this occurs, the filter switch sensor may cause the safety power switch 106 to break the electrical connection. This may prevent dangerous levels of ultraviolet light from exiting the ventilation hood plenum 18, for example.

As another example, the safety power switch 106 may break the electrical connection in response to a signal received from a pressure switch sensor. This pressure switch sensor may monitor the pressure in the duct system 34 and/or the ventilation exhaust outlets 22 so as to determine whether a blockage has occurred. If this occurs, the pressure switch sensor may cause the safety power switch 106 to break the electrical connection.

As a further example, the safety power switch 106 may break the electrical connection in response to a signal received from a fan switch sensor. This fan switch sensor may determine whether a ventilation hood plenum fan and/or an exhaust fan is operating. If the fan is not operating, the fan switch sensor may cause the safety power switch 106 to break the electrical connection. This may prevent dangerous levels of oxidizing gas from entering the kitchen, for example.

The light power module 54 may include any number of safety interlock switches 106. For example, the light power module 54 may include a safety interlock switch 106 for each type of sensor. As an example of this, the light power module 54 may include three or more safety interlock switches 106: a first safety interlock switch 106 for the filter switch sensor, a second safety interlock switch 106 for the pressure switch sensor, a third safety interlock switch 106 for the fan switch sensor, and one or more other safety interlock switches 106 for any other type(s) of sensors. As another example, more than one safety interlock switch 106 (such as all of them) may be in communication with more than one sensor (such as all of them). As such, if a sensor senses a problem, the sensor may cause all of its connected safety interlock switches 106 to break their electrical connection.

Modifications, additions, combinations, or omissions may be made to the light power module 54 of FIG. 3 without departing from the scope of the disclosure.

This specification has been written with reference to various non-limiting and non-exhaustive embodiments or examples. However, it will be recognized by persons having ordinary skill in the art that various substitutions, modifications, or combinations of any of the disclosed embodiments or examples (or portions thereof) may be made within the scope of this specification. Thus, it is contemplated and understood that this specification supports additional embodiments or examples not expressly set forth in this specification. Such embodiments or examples may be obtained, for example, by combining, modifying, or reorganizing any of the disclosed steps, components, elements, features, aspects, characteristics, limitations, and the like, of the various non-limiting and non-exhaustive embodiments or examples described in this specification. In this manner, Applicant reserves the right to amend the claims during prosecution to add features as variously described in this specification.

What is claimed is:

1. A ventilation system, comprising:
    a ventilation hood plenum coupled to a ventilation exhaust outlet; and
    an ultraviolet light system, comprising:
        an ultraviolet light source coupled inside of the ventilation hood plenum;
        a light power module, comprising:
            a base coupled to an outside surface of a wall of the ventilation hood plenum; and
            a light connector extending out of the base, the light connector further extending into the inside of the ventilation hood plenum through the wall of the ventilation hood plenum; and
        a light wire positioned entirely within the ventilation hood plenum, the light wire having a first end coupled to the ultraviolet light source, and further having a second end coupled to the light connector.

2. The system of claim 1, wherein:
    the light power module further comprises a ballast connector extending out of the base; and
    the ultraviolet light system further comprises:
        a ballast coupled to the ventilation system in a position outside of the ventilation hood plenum; and
        a ballast wire positioned outside of the ventilation hood plenum, the ballast wire having a first end that is coupled to the ballast, and further having a second end that is coupled to the ballast connector.

3. The system of claim 2, wherein the light power module further comprises a plurality of safety interlock switches that are configured to disconnect a supply of power from the ballast to the ultraviolet light source in response to a signal received from one or more sensors positioned inside or adjacent the ventilation hood plenum.

4. The system of claim 1, wherein the first end of the light wire is undetachably coupled to the ultraviolet light source.

5. The system of claim 1, wherein the first end of the light wire is detachably coupled to the ultraviolet light source.

6. The system of claim 1, further comprising a flexible shield positioned entirely within the ventilation hood plenum, the flexible shield enclosing at least a portion of the light connector and further enclosing at least a portion of the light wire.

7. The system of claim 6, wherein the flexible shield is made of silicone, urethane, thermoplastic elastomers, rubber, synthetic rubber, fabric, glass fiber, aramid fiber, or carbon fiber.

8. The system of claim 1, wherein the ventilation system further comprises one or more grease baffles positioned at least partially inside of the ventilation hood plenum, wherein the ultraviolet light source is coupled inside of the ventilation hood plenum in a location in-between the grease baffles and the ventilation exhaust outlet.

9. An ultraviolet light system, comprising:
    an ultraviolet light source configured to be coupled inside of a ventilation hood plenum;
    a light power module, comprising:
        a base configured to be coupled to an outside surface of a wall of the ventilation hood plenum; and
        a light connector extending out of the base, the light connector being configured to extend into the inside of the ventilation hood plenum through the wall of the ventilation hood plenum; and
    a light wire positionable entirely within the ventilation hood plenum, the light wire having a first end configured to be coupled to the ultraviolet light source, and further having a second end that is configured to be coupled to the light connector.

10. The system of claim 9, wherein:
    the light power module further comprises a ballast connector extending out of the base; and
    the ultraviolet light system further comprises:
        a ballast configured to be coupled to a ventilation system in a position outside of the ventilation hood plenum; and
        a ballast wire positionable outside of the ventilation hood plenum, the ballast wire having a first end that is configured to be coupled to the ballast, and further having a second end that is configured to be coupled to the ballast connector.

11. The system of claim 9, wherein the first end of the light wire is configured to be detachably coupled to the ultraviolet light source.

12. The system of claim 9, further comprising a flexible shield positionable entirely within the ventilation hood plenum, the flexible shield being configured to enclose at least a portion of the light connector and further configured to enclose at least a portion of the light wire.

13. The system of claim 12, wherein the flexible shield is made of silicone, urethane, thermoplastic elastomers, rubber, synthetic rubber, fabric, glass fiber, aramid fiber, or carbon fiber.

14. A method, comprising:
    coupling an ultraviolet light source inside of a ventilation hood plenum;
    coupling a base of a light power module to an outside surface of a wall of the ventilation hood plenum, the light power module further comprising a light connector extending out of the base, the light connector further extending into the inside of the ventilation hood plenum through the wall of the ventilation hood plenum; and
    positioning a light wire entirely within the ventilation hood plenum, the light wire having a first end that is coupled to the ultraviolet light source, and further having a second end that is coupled to the light connector.

15. The method of claim 14, wherein:
    the light power module further comprises a ballast connector extending out of the base; and the method further comprises:
coupling a ballast to a ventilation system in a position outside of the ventilation hood plenum;
coupling a first end of a ballast wire to the ballast; and
coupling a second end of the ballast wire to the ballast connector, wherein the ballast wire is positioned entirely outside of the ventilation hood plenum.

16. The method of claim 14, wherein the first end of the light wire is undetachably coupled to the ultraviolet light source.

17. The method of claim 14, wherein the first end of the light wire is detachably coupled to the ultraviolet light source.

18. The method of claim 14, further comprising positioning a flexible shield entirely within the ventilation hood plenum, the flexible shield enclosing at least a portion of the light connector and further enclosing at least a portion of the light wire.

19. The method of claim 18, wherein the flexible shield is made of silicone, urethane, thermoplastic elastomers, rubber, synthetic rubber, fabric, glass fiber, aramid fiber, or carbon fiber.

20. The method of claim 14, wherein:
one or more grease baffles are positioned at least partially inside of the ventilation hood plenum;
a ventilation exhaust outlet is coupled to the ventilation hood plenum; and
the method further comprises coupling the ultraviolet light source inside of the ventilation hood plenum in a location in-between the grease baffles and the ventilation exhaust outlet.

21. A ventilation system, comprising:
a ventilation hood plenum coupled to a ventilation exhaust outlet;
one or more ultraviolet light sources coupled inside of the ventilation hood plenum;
a conduit coupled to an outside surface of a wall of the ventilation hood plenum; and
one or more light wires positioned inside the ventilation hood plenum, each of the light wires further extending through the conduit to a position outside of the ventilation hood plenum, each of the light wires having a first end that is coupled to a respective ultraviolet light source.

22. The ventilation system of claim 21, wherein each of the light wires has a second end that is coupled to a ballast outside of the ventilation hood plenum, or that is coupled to a light connector of a light power module outside of the ventilation hood plenum.

23. The ventilation system of claim 21, wherein the conduit is a sealed conduit fitting.

* * * * *